US008888709B2

(12) United States Patent
Shuros et al.

(10) Patent No.: US 8,888,709 B2
(45) Date of Patent: Nov. 18, 2014

(54) METHOD AND APPARATUS FOR SENSING AND AVOIDING CARDIAC CONDUCTION SYSTEM DURING VALVE DEPLOYMENT

(71) Applicant: Boston Scientific Scimed, Inc., Maple Grove, MN (US)

(72) Inventors: Allan C. Shuros, St. Paul, MN (US); Joel P. Grover, St. Paul, MN (US); Ismail Guler, Maple Grove, MN (US); Adam Grovender, Brooklyn Park, MN (US); Richard Charles Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/024,294

(22) Filed: Sep. 11, 2013

(65) Prior Publication Data
US 2014/0073978 A1    Mar. 13, 2014

Related U.S. Application Data

(60) Provisional application No. 61/700,242, filed on Sep. 12, 2012.

(51) Int. Cl.
| | | |
|---|---|---|
| A61B 5/02 | (2006.01) | |
| A61B 5/04 | (2006.01) | |
| A61B 5/042 | (2006.01) | |
| A61B 5/00 | (2006.01) | |
| A61F 2/24 | (2006.01) | |
| A61B 5/06 | (2006.01) | |
| A61B 5/0452 | (2006.01) | |

(52) U.S. Cl.
CPC ............ *A61B 5/02* (2013.01); *A61B 5/0422* (2013.01); *A61F 2/2427* (2013.01); *A61B 2562/046* (2013.01); *A61B 5/6851* (2013.01); *A61F 2/2418* (2013.01); *A61B 5/066* (2013.01); *A61B 5/686* (2013.01); *A61B 5/065* (2013.01); *A61B 5/6853* (2013.01); *A61B 5/04525* (2013.01)
USPC .......................................... 600/508; 600/509

(58) Field of Classification Search
CPC ..................... A61B 2018/00839; A61N 1/3627
USPC ................................................... 600/508–509
See application file for complete search history.

(56) References Cited

U.S. PATENT DOCUMENTS

| | | |
|---|---|---|
| 5,250,071 A | 10/1993 | Palermo |
| 5,261,916 A | 11/1993 | Engelson |

(Continued)

FOREIGN PATENT DOCUMENTS

WO     WO-2014043235 A1    3/2014

OTHER PUBLICATIONS

Calvi, Valeria, et al., "Incidence rate and predictors of permanent pacemaker implantation after transcatheter aortic valve implantation with self-expanding CoreValve prosthesis", J Interv Card Electrophysiol, (2011), 7 pgs.

(Continued)

*Primary Examiner* — Nicole F Lavert
(74) *Attorney, Agent, or Firm* — Schwegman Lundberg & Woessner, P.A.

(57) ABSTRACT

Various techniques are described for replacement heart valve implantation. In one example, a system includes a specialized conduction system tissue activation potential sensing device, configured for delivery to an intracardiac region, a specialized conduction system tissue activation detector circuit, configured to detect, using the sensing device, a specialized conduction system tissue activation potential, and a processor circuit, configured to use information about the detected specialized conduction system tissue activation potential to generate a heart valve placement indication.

20 Claims, 9 Drawing Sheets

(56) References Cited

U.S. PATENT DOCUMENTS

| | | |
|---|---|---|
| 5,799,350 A * | 9/1998 | Ferek-Petric et al. .......... 607/17 |
| 5,954,761 A | 9/1999 | Machek et al. |
| 6,190,373 B1 | 2/2001 | Palermo et al. |
| 6,228,112 B1 * | 5/2001 | Klootz et al. ............... 623/2.25 |
| 6,501,983 B1 | 12/2002 | Natarajan et al. |
| 6,699,200 B2 | 3/2004 | Cao et al. |
| 7,245,973 B2 | 7/2007 | Liu et al. |
| 7,643,879 B2 | 1/2010 | Shuros et al. |
| 7,914,576 B2 | 3/2011 | Navia et al. |
| 7,917,230 B2 | 3/2011 | Bly |
| 7,988,726 B2 | 8/2011 | Langberg et al. |
| 7,996,058 B2 | 8/2011 | Ben-Haim et al. |
| 8,050,774 B2 | 11/2011 | Kveen et al. |
| 2003/0139668 A1 | 7/2003 | Ben-haim et al. |
| 2005/0137688 A1 | 6/2005 | Salahieh et al. |
| 2006/0173504 A1 | 8/2006 | Zhu et al. |
| 2006/0173505 A1 | 8/2006 | Salo et al. |
| 2007/0106357 A1 | 5/2007 | Denker et al. |
| 2007/0173861 A1 | 7/2007 | Strommer et al. |
| 2008/0027483 A1 | 1/2008 | Cartledge et al. |
| 2008/0109054 A1 | 5/2008 | Hastings et al. |
| 2009/0177090 A1 | 7/2009 | Grunwald et al. |
| 2009/0234407 A1 | 9/2009 | Hastings et al. |
| 2010/0100144 A1 | 4/2010 | Shuros et al. |
| 2010/0217119 A1 | 8/2010 | Forster et al. |
| 2012/0046740 A1 | 2/2012 | Paul et al. |

OTHER PUBLICATIONS

Massing, G. K, et al., "Anatomical configuration of the His bundle and bundle branches in the human heart", Circulation, 53(4), (Apr. 1976), 609-21.

Narula, O. S, "Longitudinal dissociation in the His bundle. Bundle branch block due to asynchronous conduction within the His bundle in man", Circulation, 56(6), (Dec. 1977), 996-1006.

Schneider, J. F, et al., "Newly acquired left bundle-branch block: the Framingham study", Ann Intern Med., 90(3), (Mar. 1979), 303-10.

"International Application Serial No. PCT/US2013/059264, International Search Report mailed Dec. 2, 2013", 5 pgs.

"International Application Serial No. PCT/US2013/059264, Written Opinion mailed Dec. 2, 2013", 6 pgs.

Rose, Alan G. et al., "The Bundle of His in Prosthetic Heart Valve Replacement", South African medical journal = Suid-Afrikaanse tydskrif vir geneeskunde, (Jan. 27, 1973).

* cited by examiner

METHOD AND APPARATUS FOR SENSING AND AVOIDING CARDIAC CONDUCTION SYSTEM DURING VALVE DEPLOYMENT

CLAIM OF PRIORITY

This application claims the benefit of priority under 35 U.S.C. §119(e) of Shuros et al., U.S. Provisional Patent Application Ser. No. 61/700,242, entitled "METHOD AND APPARATUS FOR SENSING AND AVOIDING CARDIAC CONDUCTION SYSTEM DURING VALVE DEPLOYMENT", filed on Sep. 12, 2012, which is herein incorporated by reference in its entirety.

TECHNICAL FIELD

The disclosure relates generally to medical devices and, more particularly, to replacement heart valve implantation.

BACKGROUND

A heart is the center of a person's circulatory system. It includes a complex electro-mechanical system performing two major pumping functions. The heart includes four chambers: right atrium (RA), right ventricle (RV), left atrium (LA), and left ventricle (LV). The left portions of the heart, including the LA and LV, draw oxygenated blood from the lungs and pump it to the organs of the body to provide the organs with their metabolic needs for oxygen. The right portions of the heart, including the RA and RV, draw deoxygenated blood from the body organs and pump it to the lungs where the blood gets oxygenated. These mechanical pumping functions are accomplished by contractions of the heart.

In a normal heart, the sinoatrial (SA) node, the heart's natural pacemaker, generates electrical impulses, called action potentials, that propagate through an electrical conduction system to various regions of the heart to excite the muscular tissues of these regions. Coordinated delays in the propagations of these electrical impulses in a normal electrical conduction system cause the various portions of the heart to contract in synchrony to result in efficient pumping functions. A blocked or otherwise abnormal electrical conduction system and/or a deteriorated myocardium cause asynchronized contraction of the heart. Consequently, the person suffers from poor hemodynamic performance, including poor pumping efficiency and diminished blood supply that is usable to satisfy the needs for normal metabolism of the organs.

The heart's electrical conduction system includes internodal pathways between the SA node and the atrioventricular (AV) node, the AV node, the His Bundle (also known as the Bundle of His, the AV bundle, and the Common bundle), and the Purkinje system including the right bundle branch (RBB) and the left bundle branch (LBB). In the normal heart, the electrical impulses generated from the SA node are conducted to the AV node through the internodal pathways. The propagation of the electrical impulses is delayed in the AV node. The His Bundle conducts the electrical impulses from the AV node to the right bundle branch (RBB) and left bundle branch (LBB). The RBB and LBB then conduct the electrical impulses to the RV and LV, respectively, through the Purkinje system, resulting in the contraction of the ventricles.

OVERVIEW

In general, this disclosure describes techniques for detecting a specialized cardiac conduction system signal, e.g., His Bundle potential associated with the His Bundle or signals associated with other specialized conduction tissue including the right and/or left bundle branches and their further subdivisions (fascicles), prior to deployment of a replacement heart valve, and using information about the detected specialized cardiac conduction signal during placement of the heart valve. The present inventors have recognized, among other things, that by detecting for a specialized cardiac conduction signal during delivery of a heart valve, and using information about the detected specialized cardiac conduction signal during placement of the heart valve, cardiac conduction disorders, e.g., left bundle branch block, can be avoided. Cardiac conduction disorders can increase patient mortality, especially in patients with existing heart disorders. Thus, the techniques of this disclosure can help avoid cardiac conduction disorders, such as chronic block of the cardiac conduction system, and can improve patient survival.

In one example, the disclosure provides a system comprising a specialized conduction system tissue activation potential sensing device, configured for delivery to an intracardiac region, a specialized conduction system tissue activation detector circuit, configured to detect, using the sensing device, a specialized conduction system tissue activation potential, and a processor circuit, configured to use information about the detected specialized conduction system tissue activation potential to generate a heart valve placement indication.

In another example, the disclosure provides a method comprising delivering a specialized conduction system tissue activation potential sensing device to an intracardiac region, detecting, using the specialized conduction system tissue activation potential sensing device, a specialized conduction system tissue activation potential, and determining heart valve placement information using information about the detected specialized conduction system tissue activation potential.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The His Bundle of the specialized cardiac conduction system is located on the membranous septum separating the right and left ventricles. Immediately after bifurcating with the His Bundle, the Left Bundle Branch penetrates the upper part of the muscular septum where it is then located on the endocardial surface of the left ventricle (LV). It is in this location that the conduction fibers may be susceptible to interaction with valve implantation devices, e.g., transcatheter aortic valve implantation (TAVI) devices, which can be associated with increased risk of developing cardiac conduction disorders following deployment.

Stretching of tissue, tissue inflammation, or simply metal-to-tissue contact following TAVI deployment can disrupt propagation of a cardiac conduction (or activation) signal through the conduction system. Cardiac conduction disorders can increase patient mortality, especially in patients with existing cardiac disorders, such as ischemic disease, cardiac hypertrophy from hypertension, and valve disease. Left Bundle Branch block can worsen any existing cardiac disorder.

This disclosure describes techniques for sensing a specialized cardiac conduction signal from the specialized cardiac conduction system, e.g., the His Bundle, Right Bundle Branch (RBB), the Left Bundle Branch (LBB), and/or their further subdivisions (fascicles), during deployment of a valve implantation device, e.g., TAVI device, and using information about the sensed signal during placement of the heart valve. If a specialized cardiac conduction system electrogram is sensed, the valve apparatus can be repositioned away from the specialized cardiac conduction system and chronic block of the conduction system can be avoided. Thus, the techniques of this disclosure can help avoid cardiac conduction disorders, such as chronic block of the cardiac conduction system, and can improve patient survival.

Figure 1:
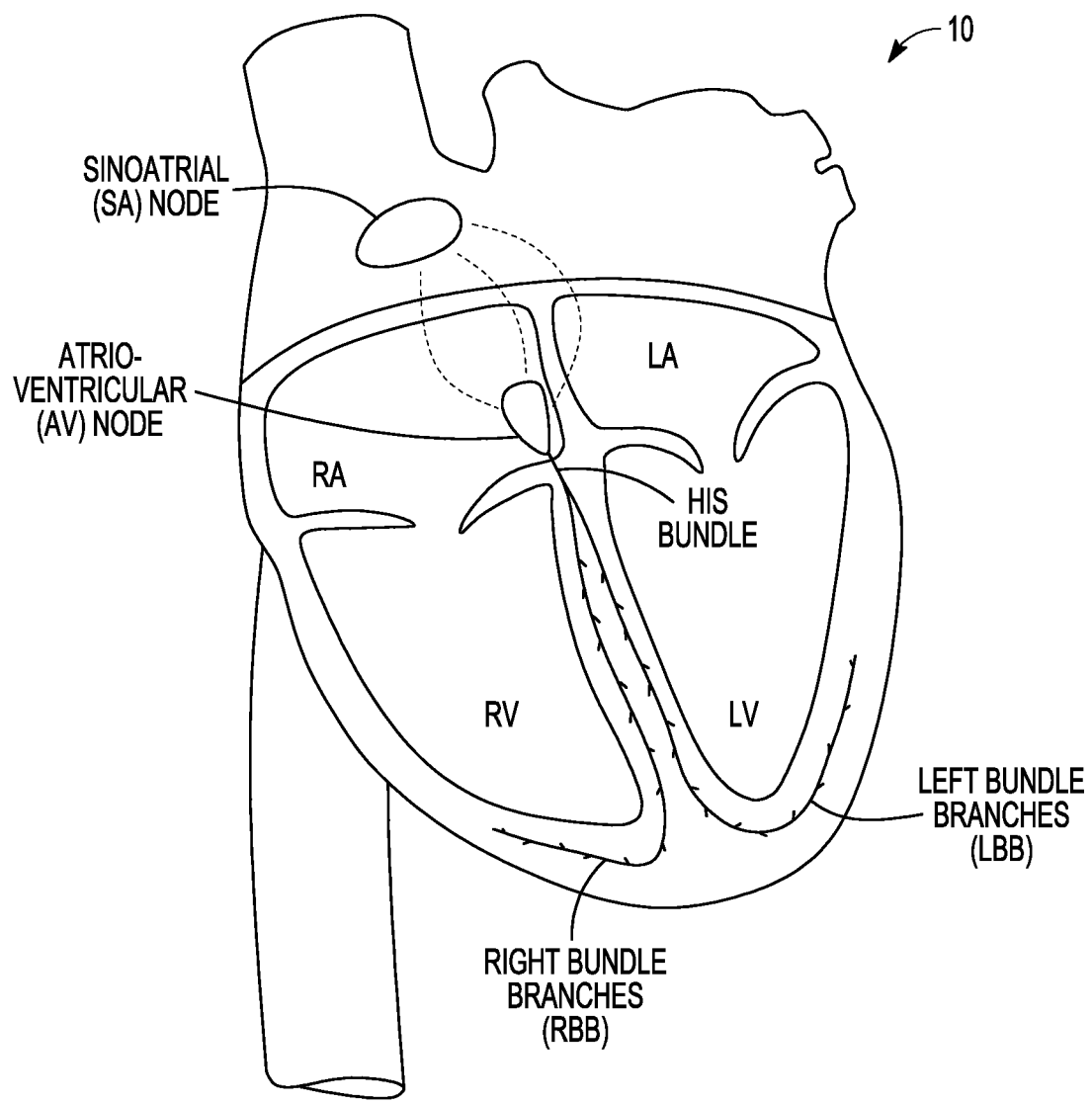
FIG. 1 is an illustration of a cardiac conduction system.

FIG. 1 is an illustration of a cardiac conduction system of a heart 10. The cardiac conduction system of heart 10 includes, among other things, the sinoatrial (SA) node, the atrioventricular (AV) node, the His Bundle, the Right Bundle Branches (RBB) and the Left Bundle Branches (LBB). The SA node in the right atrium (RA) generates electrical impulses that are conducted to the AV node through internodal pathways. The propagation of the electrical impulses is delayed in the AV node. The His Bundle conducts the electrical impulses from the AV node to the RBB and LBB. The RBB and LBB then conduct the electrical impulses to the right ventricle (RV) and left ventricle (LV), respectively, through the Purkinje system (not depicted), where the impulses activate the working myocardium, resulting in the contraction of the RV and LV.

Using various techniques of this disclosure and as described in more detail below, an activation potential sensing device configured for delivery to an intracardiac region, e.g., adjacent an aortic valve or tricuspid valve of heart 10, can sense a cardiac conduction signal from the specialized cardiac conduction system, e.g., the His Bundle, RBB, the LBB, and/or their further subdivisions (fascicles) during deployment of a valve implantation device, e.g., a TAVI device or other valve implantation device. An activation detector circuit can detect, using the sensing device, an activation potential, e.g., His Bundle activation potential, and a processor circuit can use information about the detected activation potential to generate a heart valve placement indication to a clinician. In this manner, cardiac conduction disorders, such as chronic block of the cardiac conduction system, can be avoided, thereby improving patient survival.

Figure 2:
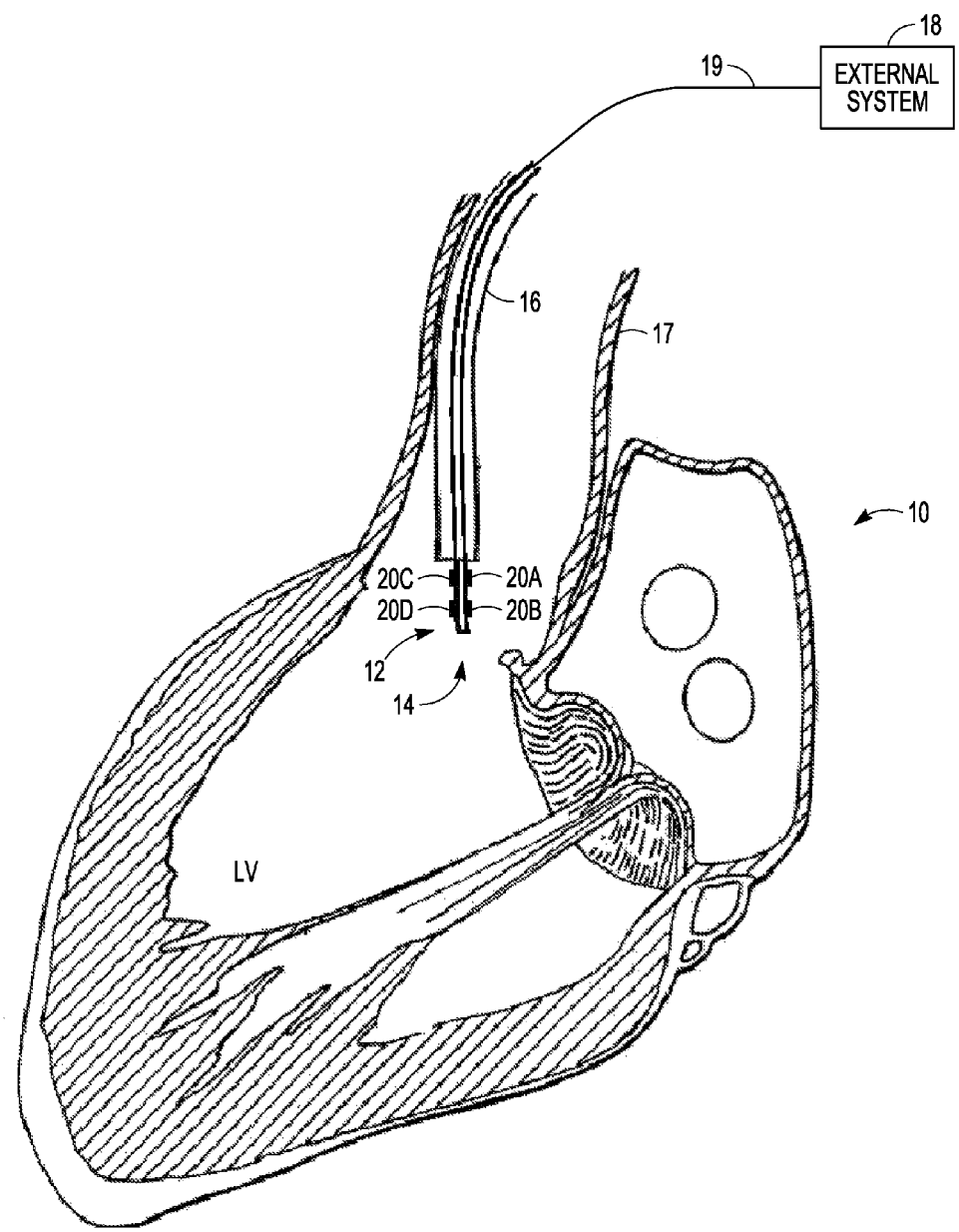
FIG. 2 is an illustration of a specialized conduction system tissue activation potential sensing device, and portions of an environment in which it is used.

FIG. 2 is an illustration of a specialized conduction system tissue activation potential sensing device, and portions of an environment in which it is used. More particularly, FIG. 2 depicts a specialized conduction system tissue activation potential sensing device (also referred to in this disclosure as a "sensing device"), shown generally at 12, that is delivered to an intracardiac region, e.g., positioned adjacent the aortic valve 14 of the heart 10. As shown and described in more detail below with respect to FIGS. 6-8, the sensing device 12 can be, for example, formed from a delivery wire, an inflatable balloon, or the replacement valve itself. In example implementations in which the sensing device 12 is an inflatable balloon or the replacement valve itself, the sensing device 12 can be delivered via a guide catheter 16 that is inserted through the aorta 17 to an intracardiac region adjacent the aortic valve of the heart 10.

The sensing device 12 can include one or more pairs of electrodes that are arranged in a bipolar configuration for electrophysiological mapping of the intracardiac region. The electrophysiological mapping of the intracardiac region allows detection of the any cardiac conduction signal from the specialized cardiac conduction system. In response to the electrophysiological mapping of the intracardiac region, a replacement valve can be accurately positioned to avoid a block of the conduction system. As described in more detail below with respect to FIG. 4, the sensing device 12 is in communication with an external system 18 via a communication link 19. The external system 18 is configured to detect, using the sensing device 12, a His Bundle activation potential to generate a heart valve placement indication.

In the example depicted in FIG. 2, the sensing device 12 can include four electrodes, e.g., electrodes 20A-20D (collectively referred as "electrodes 20"). In some examples, the sensing device 12 can include less than four electrodes. In one example, the electrodes can be spaced apart from one another in a range of about 2 millimeters (mm) to about 5 mm.

In other examples, the sensing device 12 can include two or more electrodes. In an example configuration, the electrodes 20A, 20B can form a first pair of electrodes arranged in a bipolar configuration and the electrodes 20C, 20D can form a second pair of electrodes arranged in a bipolar configuration, such that the pair(s) of electrodes are positioned with respect to a circumference of the sensing device 12. In another example configuration, the electrodes 20A, 20C can form a first pair of electrodes arranged in a bipolar configuration and the electrodes 20B, 20D can form a second pair of electrodes arranged in a bipolar configuration, such that the pair(s) of electrodes are positioned with respect to a longitudinal axis of the sensing device 12.

Using various techniques of this disclosure, a clinician, e.g., physician, can position the sensing device 12 adjacent a valve, e.g., adjacent the membranous septal and muscular septal areas, prior to deploying a replacement valve apparatus. The sensing device 12 can perform electrophysiological mapping of the region adjacent the valve and the external system 18 can sense electrograms. If present, the specialized conduction tissue activation potential, e.g., His Bundle activation potential or activation potentials associated with the RBB, LBB, and their further subdivisions (fascicles), can be identified by the morphology of the sensed electrogram, e.g., a very narrow and high frequency signal. Upon detecting the specialized conduction system tissue activation potential, the replacement valve device can be repositioned to avoid cardiac conduction electrical activity and thus minimize the possibility of LBB block.

Although the techniques of this disclosure are described above with respect to an aortic valve and TAVI devices, the techniques of this disclosure are not so limited. Rather, the techniques of this disclosure can also be used in conjunction with tricuspid valve replacement devices, for example.

Figure 3:
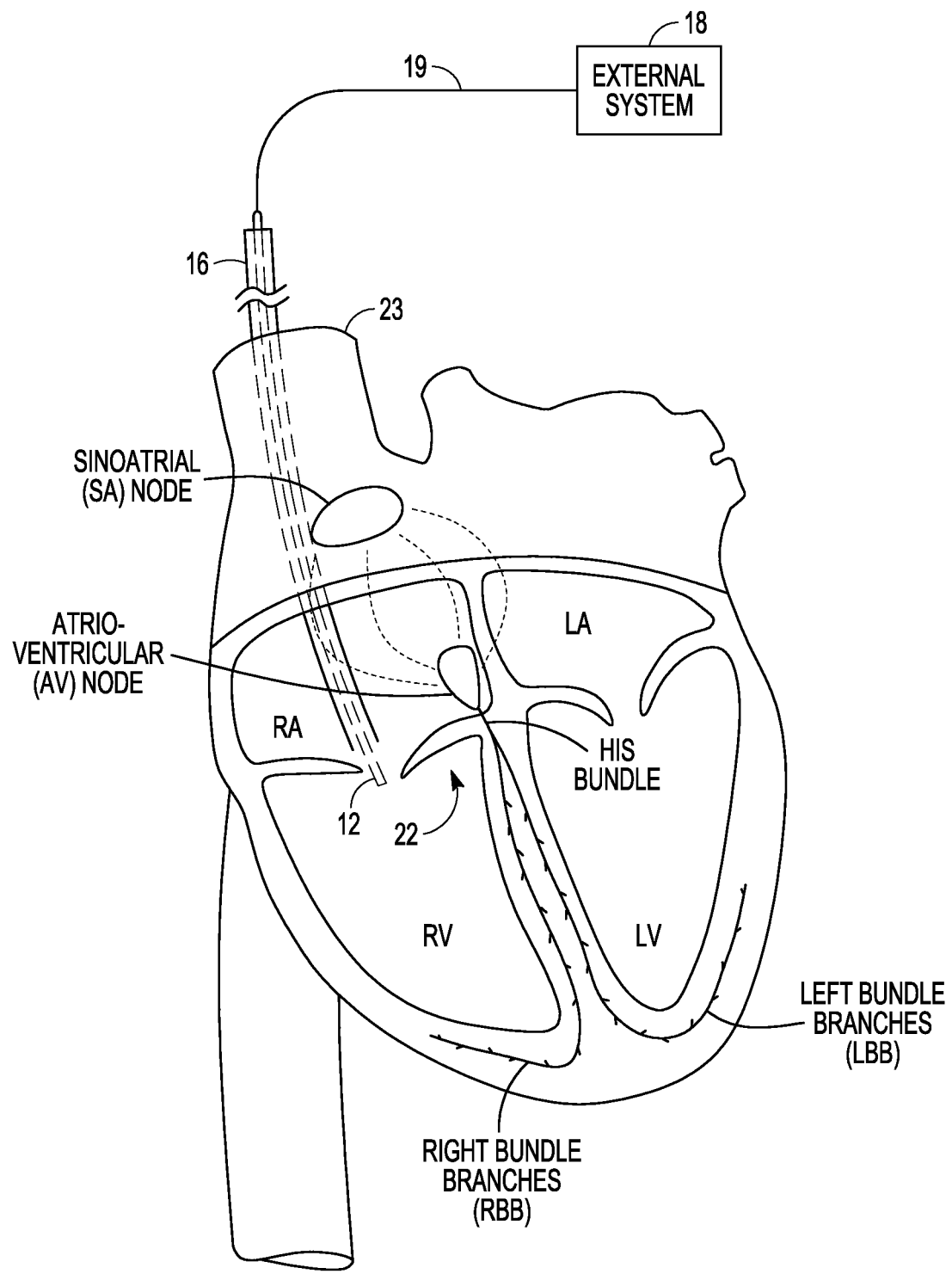
FIG. 3 is an illustration of a specialized conduction system tissue activation potential sensing device, and portions of an environment in which it is used.

FIG. 3 is an illustration of a specialized conduction system tissue activation potential sensing device, and portions of an environment in which it is used. More particularly, FIG. 3 depicts the sensing device 12 delivered to another intracardiac region, e.g., positioned adjacent the tricuspid valve 22 of the heart 10. In other implementations, the sensing device 12 can also be positioned adjacent the pulmonary valve or the aortic valve of the heart 10. As shown and described in more detail below with respect to FIGS. 6-8, the sensing device 12 can be, for example, formed from a delivery wire, an inflatable balloon, or the replacement valve itself. In examples in which the sensing device 12 is an inflatable balloon or the replacement valve device itself, the sensing device 12 can be delivered via a guide catheter 16 inserted through the superior vena cava (SVC) 23 to an intracardiac region adjacent the tricuspid valve of the heart 10.

As shown and described above with respect to FIG. 2, the sensing device 12 can include two or more pairs of electrodes that are arranged in a bipolar configuration for electrophysiological mapping of the intracardiac region. The sensing device 12 is in communication with an external system 18 that is configured to detect, using the sensing device 12, a specialized conduction system tissue activation potential to generate a heart valve placement indication.

Figure 4:
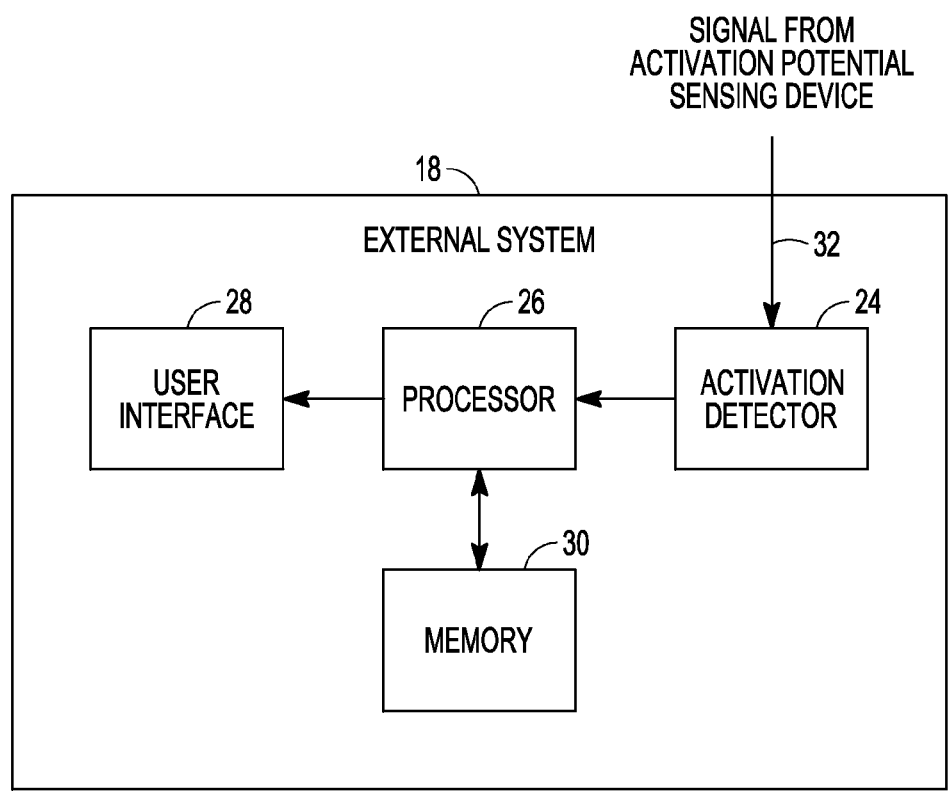
FIG. 4 is a block diagram illustrating various example components of an example system for locating the specialized conduction system tissue e by electrophysiological mapping using a specialized conduction system tissue activation potential sensing device.

FIG. 4 is a block diagram illustrating various example components of an example system for locating the specialized conduction system tissue by electrophysiological mapping using a specialized conduction system tissue activation potential sensing device. The external system 18 can include a specialized conduction system tissue activation detector circuit 24, a processor circuit 26, a user interface 28, and a memory device 30. The specialized conduction system tissue activation detector circuit 24 is configured to detect, using the sensing device 12, a specialized conduction system tissue activation potential, e.g., His Bundle activation potential. The processor circuit 26 is configured to use information about the detected specialized conduction system tissue activation potential to generate a heart valve placement indication.

As seen in FIG. 4, the external system 18 and, in particular, the specialized conduction system tissue activation detector circuit 24, via an input (not depicted), a signal 32 from the sensing device 12. Based on the characteristics of the specialized conduction system tissue activation potential, e.g., a very narrow and high frequency signal associated with the His Bundle, the specialized conduction system tissue activation detector circuit 24 can generate an electrogram and detect from the electrogram the presence or absence of a specialized conduction system tissue activation potential. The specialized conduction system tissue activation detector circuit 24 can generate an output signal that includes the electrogram information derived from the signal 32 to the processor circuit 26.

The processor circuit 26 receives the electrogram information from the specialized conduction system tissue activation detector circuit 24 and can use the electrogram information about any detected specialized conduction system tissue activation potential to generate and output a heart valve placement indication to the user interface 28. The user interface 28 can include a visual display and/or an audio speaker.

In one example, the processor circuit 26 can generate and output a heart valve placement indication that includes an image representative of the detected specialized conduction system tissue potential for display. For example, the processor circuit 26 can generate and output to the user interface 28 for display an image representative of the electrogram information received from the specialized conduction system tissue activation detector circuit 24. In one example, the image displayed on the user interface 28 can be a waveform of the electrogram that visually depicts the presence or absence of the specialized conduction system tissue activation potential. In another example, the image displayed on the user interface 28 can be a numerical value that represents one or both of the frequency and voltage of the specialized conduction system tissue activation potential.

In another example, the user interface 28 can be further configured to alert the user, e.g., clinician, of a detected specialized conduction system tissue activation potential, e.g., an audible tone and/or visual display, if the detected specialized conduction system tissue activation potential matches a specialized conduction system tissue activation potential morphology, e.g., frequency and amplitude associated with the His Bundle, RBB, and/or LBB, stored in and retrieved from the memory device 30 by the processor circuit 26. Such an example implementation can automate the detection of the specialized conduction system tissue activation potential by reducing the need for the clinician to interpret the electrogram information presented visually on the user interface 28.

If the external system 18 detects any specialized conduction system tissue activation potentials during the electrophysiological mapping procedure, then the clinician can reposition the sensing device 12 until no specialized conduction system tissue activation potentials are detected. In example implementations that utilize a delivery wire or an inflatable balloon as the sensing device 12, the location on the tissue where no specialized conduction system tissue activation potentials were detected can be identified, e.g., using fluoroscopy images. Then, using the identified location, the clinician can deliver and deploy the valve device, thereby avoiding the cardiac conduction system and minimizing the possibility of a LBB block, for example. In example implementations that utilize the valve device itself as the sensing device 12, the valve device can be deployed without the need for fluoroscopic imaging.

Figure 5A:
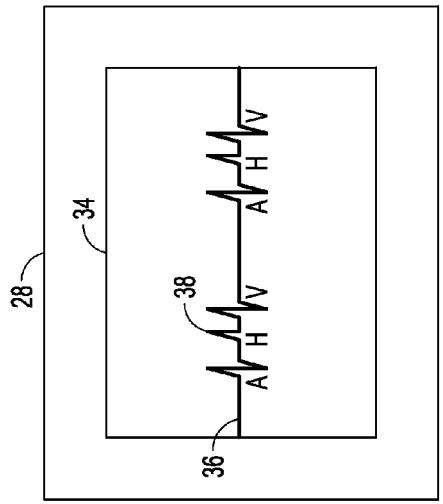
FIGS. 5A-5C are example electrograms sensed by a specialized conduction system tissue activation potential sensing device.
Figure 5B:
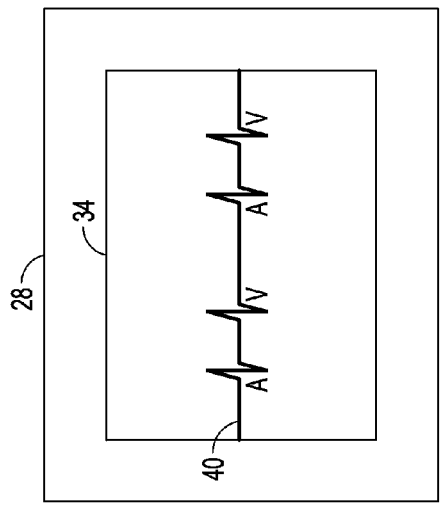
Figure 5C:
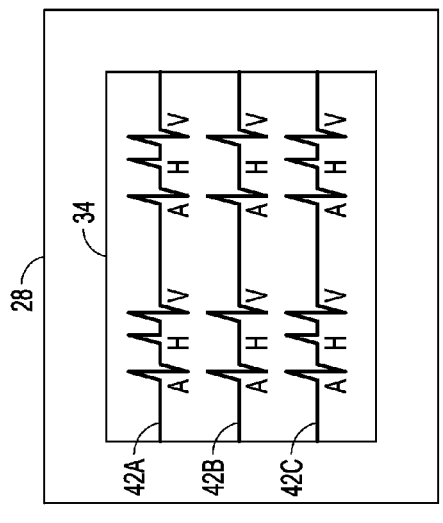

FIGS. 5A-5C are example electrograms sensed by the specialized conduction system tissue activation potential sensing device 12. As indicated above, the processor circuit 26 can generate and output to the user interface 28 for display an image representative of the electrogram information received from the specialized conduction system tissue activation detector circuit 24 via at least two pairs of electrodes of the sensing device 12. In the examples of FIGS. 5A-5C, the user interface 28 can include a display 34 that can depict one or more electrogram images that can be used as a heart valve placement indication. By way of specific example, a His Bundle activation potential is depicted in FIGS. 5A-5C. In other examples, activation potentials associated with the RBB, LBB, and/or their further subdivisions (fascicles) can be depicted and utilized similarly.

In FIG. 5A, a single electrogram 36 is depicted. The electrogram 36 can be a waveform image that depicts the presence of a His Bundle activation potential (H), shown at 38, as detected by the specialized conduction system tissue activation potential detector 24 of FIG. 4. The electrogram 36 also depicts RA depolarizations (A) and RV depolarizations (V).

FIG. 5A depicts a sequence of events. First, the RA depolarizes, then the signal propagates to the His Bundle followed by the RBB and LBB. Then the signal propagates to the terminal fibers in the ventricles, causing the ventricles to depolarize. The His Bundle/left bundle potential can be easily lost simply by moving the electrodes just a few millimeters away from the bundle while the atrial and ventricular potentials would remain. The atria and ventricles are larger structures and so their respective potential amplitudes are significantly larger compared to the bundles. The His Bundle/left bundle are small structures and the electrodes can be in almost direct contact to sense their electrical potentials.

The His Bundle can be identified by the morphology (very narrow, high frequency signal) and sequence of activation (atrial, His Bundle, then ventricle). If the left bundle potential is visible, that would indicate direct contact with the bundle which should be avoided. The clinician can then reposition the valve apparatus to a new location away from the Bundle, e.g., a few millimeters, or to a position where the struts of the valve device would not make direct contact with the Bundle.

In another example, the image displayed on the user interface 28 can be a numerical value that represents one or both of the frequency and voltage of the His Bundle activation potential. As indicated above, the user interface 28 can be further configured to alert the user, e.g., clinician, of a detected His Bundle activation potential, e.g., an audible tone and/or visual display, if the detected His Bundle activation potential matches a His Bundle activation potential morphology, e.g., frequency and amplitude, stored in and retrieved from the memory device 30 by the processor circuit 26. Such an example implementation can help automate the detection of the His Bundle activation potential by reducing the need for the clinician to interpret the electrogram information presented visually on the user interface 28.

Upon detection of the His Bundle activation potential 38, such as shown in FIG. 5A, the clinician can reposition the sensing device 12 until no His Bundle activation potentials are detected. As indicated above, in example implementations that utilize a delivery wire or an inflatable balloon as the sensing device 12, the location on the tissue where no His Bundle activation potentials were detected can be identified, e.g., using fluoroscopy images. Then, using the identified location, the clinician can deliver and deploy the valve device, thereby avoiding the cardiac conduction system and minimizing the possibility of a LBB block, for example. In example implementations that utilize the valve device itself as the sensing device 12, the valve device can be deployed without the need for fluoroscopic imaging.

In FIG. 5B, a single electrogram 40 is depicted on the display 34 of the user interface 28. The electrogram 40 can be a waveform image that depicts the absence of a His Bundle activation potential, e.g., after the clinician has repositioned the sensing device 12, as detected by the specialized conduction system tissue activation potential detector 24 of FIG. 4. The electrogram 40 depicts RA depolarizations (A) and RV depolarizations (V), without an intervening His Bundle activation potential. Because the electrogram 40 of FIG. 5B does not include a His Bundle activation potential, the clinician can identify the location of the sensing device 12 and consider the location as a viable location for delivery of the valve device.

As indicated above, the sensing device 12 can include two or more pairs of electrodes, where each pair can be used to sense for a His Bundle activation potential. In FIG. 5C, three electrograms 42A-42C are depicted on the display 34 of the user interface 28, as sensed by three pairs of electrodes. In examples that include more pairs of electrodes, additional electrograms can be depicted, e.g., along with electrograms 42A-42C, or on separate screens between which the clinician can toggle.

The electrograms 42A-42C can be waveform images that depict the presence or absence of a His Bundle activation potential (H), along with RA depolarizations (A) and RV depolarizations (V). As seen in FIG. 5C, electrograms 42A and 42C depict the presence of a His Bundle activation potential (H), while the electrogram 42B depicts the absence of a His Bundle activation potential. Based on the electrograms 42A-42C, the clinician can identify the location of the sensing device 12 as undesirable due to the presence of the His Bundle activation potential. The clinician can then adjust the position of the sensing device 12 and consider whether the new location is viable location based on newly generated electrograms. In this manner and in accordance with various techniques of this disclosure, a detected His Bundle activation potential can be used to position a heart valve device while avoiding the cardiac conduction system.

Figure 6:
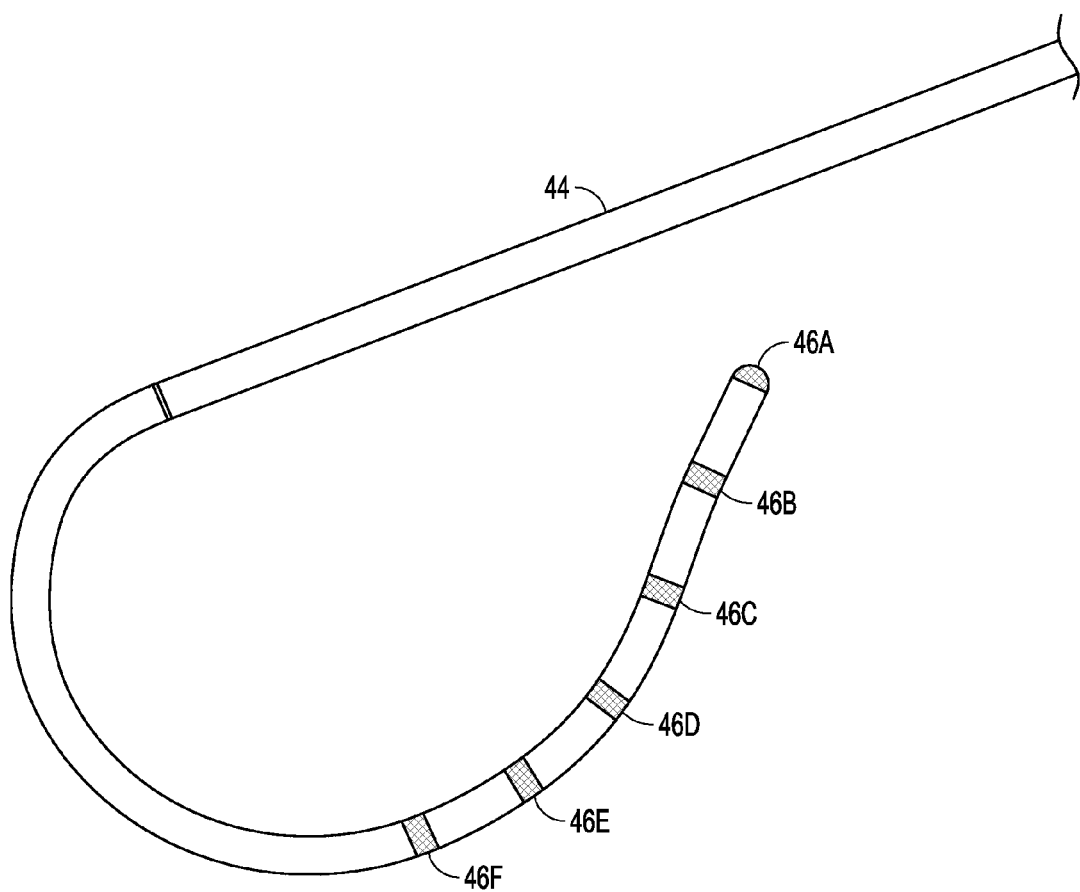
FIG. 6 is an example of the specialized conduction system tissue activation potential sensing device of FIG. 2.

FIG. 6 is an example of the specialized conduction system tissue activation potential sensing device of FIG. 2. More particularly, FIG. 6 depicts an example delivery wire 44 that can be used to sense for specialized conduction system tissue activation potentials. The delivery wire 44 can include two or more pairs of electrodes, e.g., pairs arranged from electrodes 46A-46F, that are arranged in bipolar configurations for electrophysiological mapping of an intracardiac region. Conductors (not depicted) from electrodes 46A-46F can run along the shaft of the delivery wire 44 to the external system 18 via the communication link 19. The external system 18 can use the signals detected by the pairs of electrodes to generate the electrograms shown in FIGS. 5A-5C.

In one example, the delivery wire 44 can a flexible, steerable device, e.g., guidewire, over which the replacement heart valve device can be delivered. The delivery wire 44 can be, for example, similar to the Polaris DX™ Unidirectional Steerable Diagnostic Catheter, available from Boston Scientific Corporation.

After mapping the intracardiac region of interest, the clinician can deliver the heart valve device over the delivery wire 44. Then, the clinician can remove the delivery wire 44 from the patient.

Figure 7:
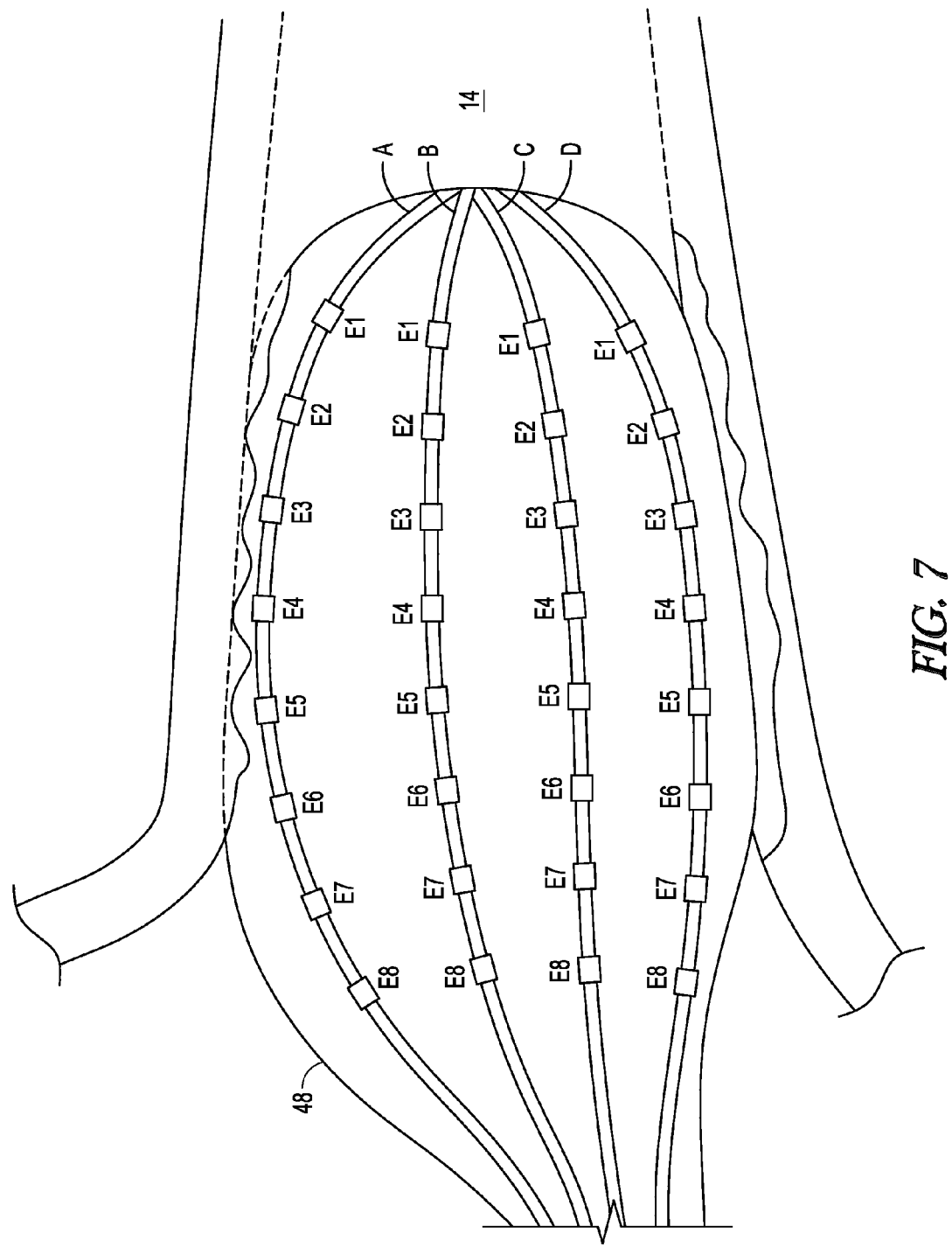
FIG. 7 is another example of the specialized conduction system tissue activation potential sensing device of FIG. 2.

FIG. 7 is another example of the specialized conduction system tissue activation potential sensing device of FIG. 2. More particularly, FIG. 7 depicts an example inflatable balloon 48, e.g., a balloon used in balloon aortic valvuloplasty (BAV) procedures, that can be used to sense for specialized conduction system tissue activation potentials. The balloon 48 can include two or more electrodes that are arranged in bipolar configurations for electrophysiological mapping of an intracardiac region, e.g., adjacent the aortic valve 14. In the specific example shown in FIG. 7, four flexible conductors A, B, C, D are disposed along on the outer surface of balloon 48 and extend proximally to the external system 18 via the communication link 19. Although four flexible conductors are depicted in FIG. 7, some examples include more or less than four conductors. Each flexible conductor can include one or more electrodes, e.g., electrodes E1-E8. In one example, the electrodes can be spaced apart from one another in a range of about 2 mm to about 5 mm. The external system 18 can use the signals detected by two or more pairs of the electrodes E1-E8 on two or more flexible conductors A-D to generate the electrograms shown in FIGS. 5A-5C.

The flexible conductor and electrode combinations form flexible sensors that can be arranged in a patterned array. These flexible sensors can be made of ultrathin ribbons of silicon and mounted on the surface of the balloon 48 to create a high resolution electrical map of the membranous septal and muscular septal areas. These flexible sensors do not compromise the folding, delivery, and expansion of the balloon. They can also keep the folded balloon profile small.

After mapping the intracardiac region of interest, the clinician can remove the balloon 48. Then, the clinician can deliver the replacement heart valve device to the intracardiac region.

Figure 8:
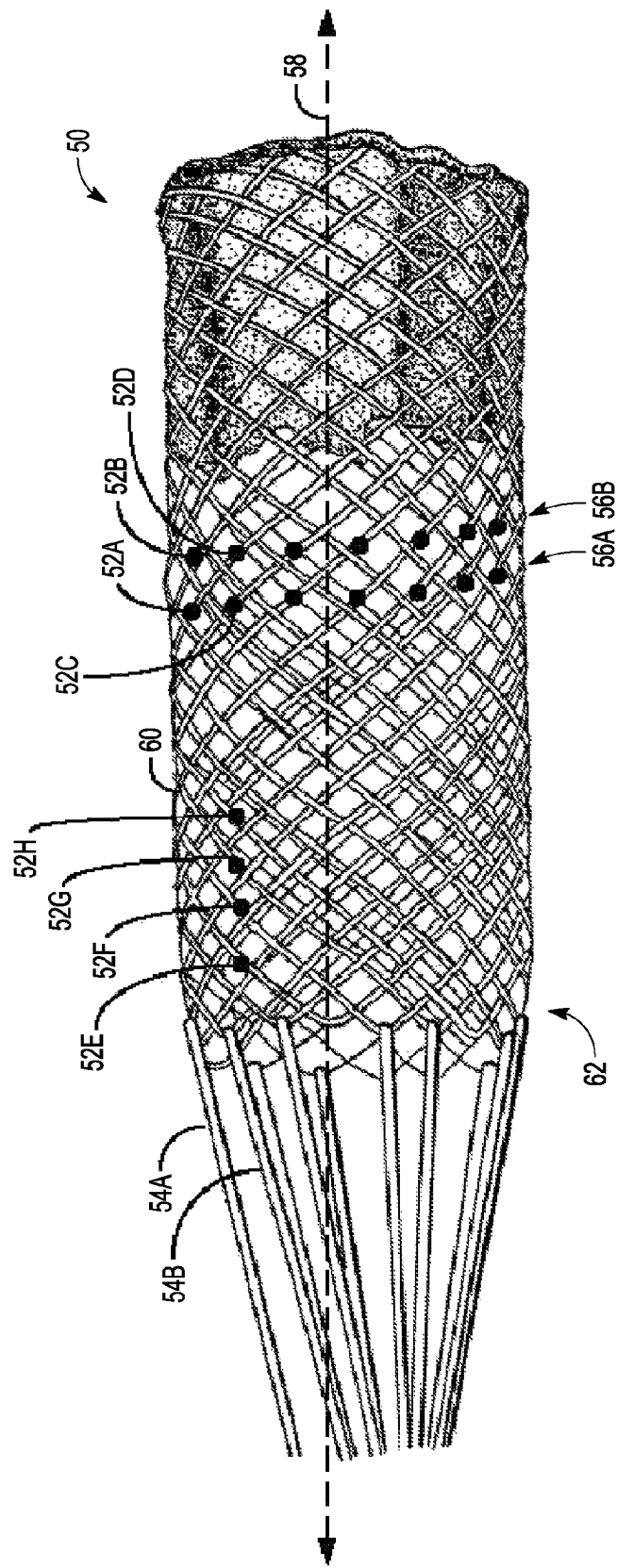
FIG. 8 is another example of the specialized conduction system tissue activation potential sensing device of FIG. 2.

FIG. 8 is another example of the specialized conduction system tissue activation potential sensing device of FIG. 2. More particularly, FIG. 8 depicts a replacement heart valve device 50 that includes electrodes, e.g., electrodes 52A-52H (collectively "electrodes 52"), that can be used to sense for specialized conduction system tissue activation potentials. The electrodes can be arranged in bipolar configurations for electrophysiological mapping of an intracardiac region. Electrical signals sensed by the electrodes on the device 50 are carried to the external system 18 via conductors, e.g., conductors 54A, 54B, (and communication link 19) that extend the length of a delivery catheter (not depicted).

In some examples, the valve device 50 can include two or more rings of electrodes, e.g., electrode rings 56A, 56B, where each ring 56A, 56B is disposed about a circumference of the valve device 50. In other examples, the valve device 50 can include two or more electrodes, e.g., electrodes 56C, 56D, that are spaced apart from one another along a longitudinal axis 58 of valve device 50. In one example, the valve device 50 can include one or more rings of electrodes disposed about a circumference of the valve device 50 and electrodes spaced apart from one another along a longitudinal axis 58 of valve device 50.

The valve device 50 can include a plurality of electrically conductive struts 60. In some examples, the struts 60 can be coated with an electrically insulative material, with portions of the insulative material removed to expose conductive regions that can define the electrodes 52. In one example, the exposed portions of the struts 60 can be positioned on the valve device 50 in regions most likely in the area of the cardiac conduction system, e.g., most apical of the valve device 50. In one example, the electrodes can be spaced apart from one another in a range of about 2 mm to about 5 mm. In some examples, a distal exterior of the valve device 50 can be coated with a lubricious material to reduce irritation of the left bundle branch.

When the valve device 50 is deployed, the cardiac conduction signals are monitored via the external system 18. If cardiac conduction signals are detected, then the clinician can reposition the valve device 50 until the cardiac conduction signals are no longer present, e.g., no longer visible on the display 34 of the user interface 28, assuming that a block has not been induced and that cardiac activation is the same as prior to the procedure. One example repositionable heart valve device 50 is shown and described in U.S. 20050137688 to Salahieh et al., titled, "REPOSITIONABLE HEART VALVE AND METHOD," the contents of which being incorporated herein in their entirety.

Once the valve device 50 has been deployed with no evidence of sensing cardiac conduction signals, then the clinician can disconnect electrical communication with the valve device 50 and remove the delivery system from the valve. Disconnection can be accomplished using several techniques.

In one example, disconnection can be accomplished by heating the valve strut and conductor interface, shown generally at 62, and melting the conductors, e.g., conductors 54A, 54B, thereby releasing the valve device 50 from the conductors. The melting of conducting wires can be achieved by the passage of an electric current through the wires that will result in Joule heating due to the ohmic resistance of the wires.

In another example, disconnection can be accomplished by mechanically detaching the valve device from the conductors 54A, 54B. For example, external system 18 can be connected to a valve delivery system handle that includes actuation elements that connect to a valve scaffold of the replacement heart valve 10 via a connector system, such as shown and described in U.S. Patent Application Publication No. 2012/0046740 to Paul et al., titled "MEDICAL DEVICES AND DELIVERY SYSTEMS FOR DELIVERING MEDICAL DEVICES," and filed on Nov. 2, 2011, now issued as U.S. Pat. No. 8,617,236, the entire content of which being incorporated herein by reference. The electrical signal pathway from the external system 18 can be completed by the connection of electrodes 52 and conductors 54, which can also function as the actuation elements. Mechanical detachment of the electrical connection can be completed by the uncoupling of the locking mechanism, as described in US 2012/0046740, now issued as U.S. Pat. No. 8,617,236, with respect with FIG. 5. Electrodes can be attached to a post of the heart valve 10. In the handle of the delivery system, the conductors can branch out to connectors to the processor 26.

Mechanical detachment can also be accomplished by an interlocking connection at a detachment zone that is locked by a sheath during the procedure and unlocked by pulling the distal end of the sheath beyond the detachment zone, similar to the mechanism used in the Interlock™ Fibered IDC (interlocking detachable coil) coils manufactured by Boston Scientific. Additional information regarding mechanical detachment techniques can be found in U.S. Pat. No. 5,250,071 to Palermo, titled "Detachable embolic coil assembly using interlocking clasps and method of use," and filed on Sep. 22, 1992, U.S. Pat. No. 5,261,916 to Engelson, titled "Detachable pusher-vasoocclusive coil assembly with interlocking ball and keyway coupling," and filed on Dec. 12, 1991, the entire contents of each being incorporated herein by reference. In another example, a connection can be released by using a mechanical pusher assembly similar to that shown and described in U.S. Pat. No. 6,190,373 to Palermo et al., titled "Axially detachable embolic coil assembly," and filed on Dec. 15, 1998, the entire contents of which being incorporated herein by reference. In another example, mechanical detachment can also be accomplished by a distal cutting device which is activated to cleave the conducting wires once a desired placement of the valve device at the target site is achieved.

In another example, disconnection can be accomplished by using electrolytic detachment techniques, e.g., anodic dissolution, similar to the InZone® Detachment System manufactured by Boston Scientific for Stryker Neurovascular.

In addition to detection and avoidance of cardiac conduction signals, the valve device 50 of FIG. 8 can be used for selectively pacing the specialized cardiac conduction system, e.g., pacing the left bundle branch. For example, if a block has been permanently induced, then artificial pacing may be delivered through the valve device 50. Electrical pacing distal to a lesion on the His bundle can correct conduction block. A pacing system can include a leadless or lead-based pulse generator connected to the valve device 50 for pacing the affected bundle branch. General pacing of a working myocardium via a heart valve device is shown and described in detail in U.S. Pat. No. 7,643,879, titled "INTEGRATED CARDIAC RHYTHM MANAGEMENT SYSTEM WITH HEART VALVE," to Shuros et al. and incorporated herein by reference in its entirety.

Figure 9:
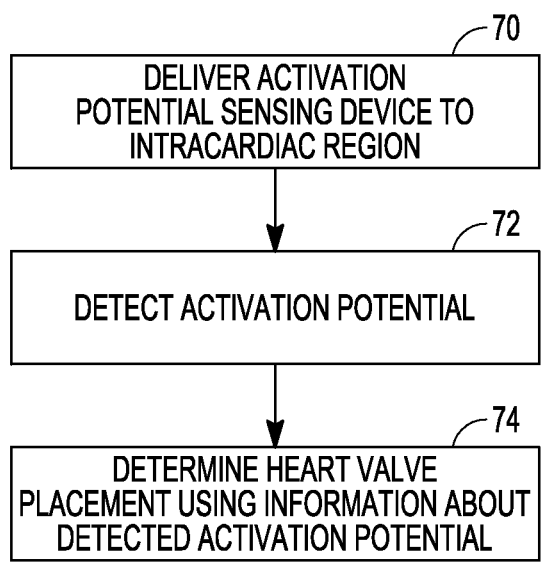
FIG. 9 is a flow diagram illustrating example operation of the system for locating the specialized conduction system tissue by electrophysiological mapping using the specialized conduction system tissue activation potential sensing device of FIG. 2.

FIG. 9 is a flow diagram illustrating example operation of the system for locating the specialized conduction system tissue by electrophysiological mapping using the specialized conduction system tissue activation potential sensing device of FIG. 2. The example method depicted in FIG. 9, includes delivering a specialized conduction system tissue activation potential sensing device to an intracardiac region (70). For example, sensing devices such as delivery wire 44 of FIG. 6, the balloon 48 of FIG. 7, or the valve device 50 of FIG. 8 can be delivered. After delivering the sensing device, the example method includes detecting, using the specialized conduction system tissue activation potential sensing device, a specialized conduction system tissue activation potential (72). For example, the specialized conduction system tissue activation detector 24 of external system 18 (FIG. 4) can detect a specialized conduction system tissue activation potential from the signal sensed by the specialized conduction system tissue activation potential sensing device. Next, the method includes determining heart valve placement information using information about the detected specialized conduction system tissue activation potential (74). For example, the processor circuit 26 of the external system 18 (FIG. 4) can receive the electrogram information from the specialized conduction system tissue activation detector circuit 24 and can use the electrogram information about any detected specialized conduction system tissue activation potential to generate and output a heart valve placement indication to the user interface 28. The user interface 28 can include a visual display and/or an audio speaker.

In the manner described above, the techniques of this disclosure can help avoid cardiac conduction disorders, such as chronic block of the cardiac conduction system, and can improve patient survival.

Various Notes & Examples

In Example 1, a system includes a specialized conduction system tissue activation potential sensing device, configured for delivery to an intracardiac region, a specialized conduction system tissue activation detector circuit, configured to detect, using the sensing device, a specialized conduction system tissue activation potential, and a processor circuit, configured to use information about the detected specialized conduction system tissue activation potential to generate a heart valve placement indication.

In Example 2, the specialized conduction system tissue potential sensing device in the system of Example 1 optionally includes one of a balloon, a delivery wire, and a replacement heart valve.

In Example 3, the replacement heart valve in the system of Example 2 optionally includes a plurality of electrically conductive struts, wherein a portion of a first one of the plurality of struts defines a first one of the pair of electrodes, and wherein a portion of a second one of the plurality of struts defines a second one of the pair of electrodes.

In Example 4, the replacement heart valve of either of Examples 2 or 3 optionally defines a longitudinal axis, and the first one of the pair of electrodes and the second one of the pair of electrodes are spaced apart from one another along the longitudinal axis.

In Example 5, the replacement heart valve of any one or more of Examples 2-4 optionally has a circumference, and wherein the first one of the pair of electrodes and the second one of the pair of electrodes are spaced apart from one another along the circumference.

In Example 6, the system of any one or more of Examples 1-5 optionally further includes a user interface configured to display an image representative of a detected specialized conduction system tissue potential.

In Example 7, the user interface of Example 6 is optionally further configured to alert a user of a detected specialized conduction system tissue potential.

In Example 8, the system of any one or more of Examples 1-7 optionally further includes a pair of electrodes in communication with the specialized conduction system tissue activation potential sensing device, a pair of conductors in communication with the pair of electrodes and the specialized conduction system tissue activation detector circuit, wherein the pair of conductors is configured to be detached from the pair of electrodes.

In Example 9, the pair of conductors in Example 8 is optionally configured to be detached from the electrodes via one of mechanical detachment, electrolytic detachment, and thermal detachment.

In Example 10, the replacement heart valve in any one or more of Examples 2-5 optionally includes a pair of pacing electrodes configured to pace a heart of the patient.

In Example 11, a method includes delivering a specialized conduction system tissue activation potential sensing device to an intracardiac region, detecting, using the specialized conduction system tissue activation potential sensing device, a specialized conduction system tissue activation potential, and determining heart valve placement information using information about the detected specialized conduction system tissue activation potential.

In Example 12, the method of Example 11 is optionally configured such that the specialized conduction system tissue potential sensing device is one of a balloon, a delivery wire, and a replacement heart valve.

In Example 13, the method of Example 12 is optionally configured such that the replacement heart valve includes a plurality of electrically conductive struts, wherein a portion of a first one of the plurality of struts defines a first one of the pair of electrodes, and wherein a portion of a second one of the plurality of struts defines a second one of the pair of electrodes.

In Example 14, the method of either of Examples 12 or 13 is optionally configured such that the replacement heart valve defines a longitudinal axis, and wherein the first one of the pair of electrodes and the second one of the pair of electrodes are spaced apart from one another along the longitudinal axis.

In Example 15, the method of any one or more of Examples 12-14 is optionally configured such that the replacement heart valve has a circumference, and wherein the first one of the pair of electrodes and the second one of the pair of electrodes are spaced apart from one another along the circumference.

In Example 16, the method of any one or more of Examples 11-15 optionally includes displaying an image representative of a detected specialized conduction system tissue potential.

In Example 17, the method of any one or more of Examples 11-16 optionally includes alerting a user in response to sensing a specialized conduction system tissue potential.

In Example 18, the method of any one or more of Examples 11-17 optionally includes detaching a pair of conductors from a pair of electrodes associated with the specialized conduction system tissue potential sensing device.

In Example 19, the method of Example 18 is optionally configured such that detaching a pair of conductors from a pair of electrodes associated with the specialized conduction system tissue potential detection device includes one of mechanical detachment, electrolytic detachment, and thermal detachment.

In Example 20, the method of any one or more of Examples 11-19 optionally includes delivering pacing pulses to a heart of the patient.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a specialized conduction system tissue activation potential sensing device, configured for delivery to an intracardiac region;
   a specialized conduction system tissue activation detector circuit, configured to detect, using the sensing device, a specialized conduction system tissue activation potential; and
   a processor circuit that generates a replacement heart valve placement indication using information about the detected specialized conduction system tissue activation potential.

2. The system of claim 1, wherein the specialized conduction system tissue potential sensing device is one of a balloon, a delivery wire, and a replacement heart valve.

3. The system of claim 1, wherein the replacement heart valve comprises a plurality of electrically conductive struts, wherein a portion of a first one of the plurality of struts defines a first one of the pair of electrodes, and wherein a portion of a second one of the plurality of struts defines a second one of the pair of electrodes.

4. The system of claim 3, wherein the replacement heart valve defines a longitudinal axis, and wherein the first one of the pair of electrodes and the second one of the pair of electrodes are spaced apart from one another along the longitudinal axis.

5. The system of claim 3, wherein the replacement heart valve has a circumference, and wherein the first one of the pair of electrodes and the second one of the pair of electrodes are spaced apart from one another along the circumference.

6. The system of claim 1, further comprising:
   a user interface configured to display an image representative of a detected specialized conduction system tissue potential.

7. The system of claim 1, wherein the user interface is further configured to alert a user of a detected specialized conduction system tissue potential.

8. The system of claim 1, further comprising:
   a pair of electrodes in communication with the specialized conduction system tissue activation potential sensing device;

a pair of conductors in communication with the pair of electrodes and the specialized conduction system tissue activation detector circuit, wherein the pair of conductors is configured to be detached from the pair of electrodes.

9. The system of claim 8, wherein the pair of conductors are configured to be detached from the electrodes via one of mechanical detachment, electrolytic detachment, and thermal detachment.

10. The system of claim 2, wherein the replacement heart valve further comprises:

a pair of pacing electrodes configured to pace a heart of the patient.

11. A method comprising:

delivering a specialized conduction system tissue activation potential sensing device to an intracardiac region;

detecting, using the specialized conduction system tissue activation potential sensing device, a specialized conduction system tissue activation potential; and generating a replacement heart valve placement indication using information about the detected specialized conduction system tissue activation potential.

12. The method of claim 11, wherein the specialized conduction system tissue potential sensing device is one of a balloon, a delivery wire, and a replacement heart valve.

13. The method of claim 12, wherein the replacement heart valve comprises a plurality of electrically conductive struts, wherein a portion of a first one of the plurality of struts defines a first one of the pair of electrodes, and wherein a portion of a second one of the plurality of struts defines a second one of the pair of electrodes.

14. The method of claim 13, wherein the replacement heart valve defines a longitudinal axis, and wherein the first one of the pair of electrodes and the second one of the pair of electrodes are spaced apart from one another along the longitudinal axis.

15. The method of claim 13, wherein the replacement heart valve has a circumference, and wherein the first one of the pair of electrodes and the second one of the pair of electrodes are spaced apart from one another along the circumference.

16. The method of claim 11, further comprising:

displaying an image representative of a detected specialized conduction system tissue potential.

17. The method of claim 11, further comprising:

alerting a user in response to sensing a specialized conduction system tissue potential.

18. The method of claim 11, further comprising:

detaching a pair of conductors from a pair of electrodes associated with the specialized conduction system tissue potential sensing device.

19. The method of claim 18, wherein detaching a pair of conductors from a pair of electrodes associated with the specialized conduction system tissue potential detection device comprises one of mechanical detachment, electrolytic detachment, and thermal detachment.

20. The method of claim 11, further comprising:

delivering pacing pulses to a heart of the patient.

* * * * *